United States Patent [19]

Miyata et al.

[11] Patent Number: 4,895,444
[45] Date of Patent: Jan. 23, 1990

[54] DETECTOR DEVICE FOR MIXING RATIO FOR GASOLINE AND ALCOHOL OR THE LIKE

[75] Inventors: Shigeru Miyata; Yoshihiro Matsubara, both of Nagoya, Japan

[73] Assignee: NGK Spark Plug Co., Ltd., Nagoya, Japan

[21] Appl. No.: 180,490

[22] Filed: Apr. 12, 1988

[30] Foreign Application Priority Data

Apr. 17, 1987 [JP] Japan .................................. 62-95962
Jun. 26, 1987 [JP] Japan .................................. 62-160242

[51] Int. Cl.⁴ ............................................. G01N 21/41
[52] U.S. Cl. .................................... 356/128; 356/136
[58] Field of Search ............... 356/128, 133, 135, 136, 356/137

[56] References Cited

U.S. PATENT DOCUMENTS 4,438,749 3/1984 Schwippert .......................... 356/133
4,749,274 6/1988 Aoki et al. ........................... 356/136

FOREIGN PATENT DOCUMENTS 2807805 10/1978 Fed. Rep. of Germany ...... 356/136

Primary Examiner—F. L. Evans
Attorney, Agent, or Firm—Cooper & Dunham

[57] ABSTRACT

A detector device for determining the mixing ratio of gasoline and alcohol includes a flint glass plate, one side of which is placed to be in direct contact with a mixing liquid of gasoline and alcohol, a light emitting diode is located at the other side of the flint glass plate to be opposite to the mixing liquid so that light beams emitted from the diode enter the flint glass plate to be incident on a boundary between the plate and the mixing liquid and a photo diode having a rectangular shape and located in coplanar relationship with the light emitting diode to receive the light beams totally reflected from the boundary. The distance between the photo diode and the light emitting diode and the width dimension of the photo diode are determined such to provide incident angles ranging from a minimum corresponding to the critical angle when the mixing liquid ratio is at lower limit of the predetermined range to a maximum corresponding to the critical angle when the mixing liquid ratio is at upper limit of the predetermined range.

7 Claims, 7 Drawing Sheets

DETECTOR DEVICE FOR MIXING RATIO FOR GASOLINE AND ALCOHOL OR THE LIKE

BACKGROUND OF THE INVENTION

1. Field of the Invention

This invention relates to a detector device in which a mixing ratio of such as, for example, gasoline and alcohol is optically measured, and suited in use for fuel of internal combustion engine.

2. Description of the Prior Art

In an internal combustion engine for motor vehicle, it has been suggested to apply a mixing liquid of gasoline and alcohol to a combustible fuel. In order to obtain a good engine output, it is necessary to continuously detect a mixing ratio of the liquid so that an automatic combustion control unit may work to insure most appropriate quantity of injection fuel.

For this purpose, a detector device is provided which comprises an optical permeable column arranged its outer whole surface to be in direct contact with a mixing liquid of gasoline and alcohol. Sight beams from a light emitting diode permeate the column through its one end and reach at a boundary between the column and the mixing liquid. The light beams incident on the boundary at less than a critical angle, is totally refracted while the light beams incident on the boundary at more than a critical angle, is totally reflected. The light beams totally reflected, go out of the column through its other end to fall on a photo diode, the output of which is in accordance with the quantity of the light beams fell upon. Since the critical angle changes depending upon the mixing degree of the liquid, measuring the output from the photo diode enables to obtain a mixing ratio of the liquid.

The device, however, places both the diodes to sandwich the column in the lengthwise direction, requiring cases to enclose those diodes discretely, and making a whole structure greater, and increasing the number of assembly processes.

Therefore, it is an object of this invention to provide a detector device which is capable of reducing a thickness and lengthwise dimension to make a whole structure compact, and cost saving, contributing to decrease of assembly processes.

According to the present invention, there is provided a detector device comprising; an optically permeable plate, one side of which is placed to be in direct contact with mixing liquid of different kinds of components; a light emitting diode located at other side of the optically permeable plate to be opposite to the mixing liquid, so that light beams emitted from the diode enter the optically permeable plate to be incident on a boundary between the plate and the mixing liquid, the light beams incident on the boundary at less than a critical angle being refracted toward the mixing liquid, while the light beams incident on the boundary at more than the critical angle being totally reflected, the critical angle depending on a degree of the mixing liquid; a photo diode having a rectangular shape, and located in coplanar relationship with the light emitting diode to receive the light beams totally reflected from the boundary to generate an output in accordance with the light beams received; and the distance between the photo diode and the light emitting diode and width dimension of the photo diode along the direction of the distance being determined such as to provide incident angles ranging from a minimum corresponding to the critical angle when the mixing liquid ratio is at lower limit of the predetermined range to a maximum corresponding to the critical angle when the mixing liquid ratio is at upper limit of the predetermined range.

DETAILED DESCRIPTION OF THE INVENTION

In reference with accompanied drawings, embodiments of this invention is described which is associated with an internal combustion engine for motor vehicle.

Figure 1:
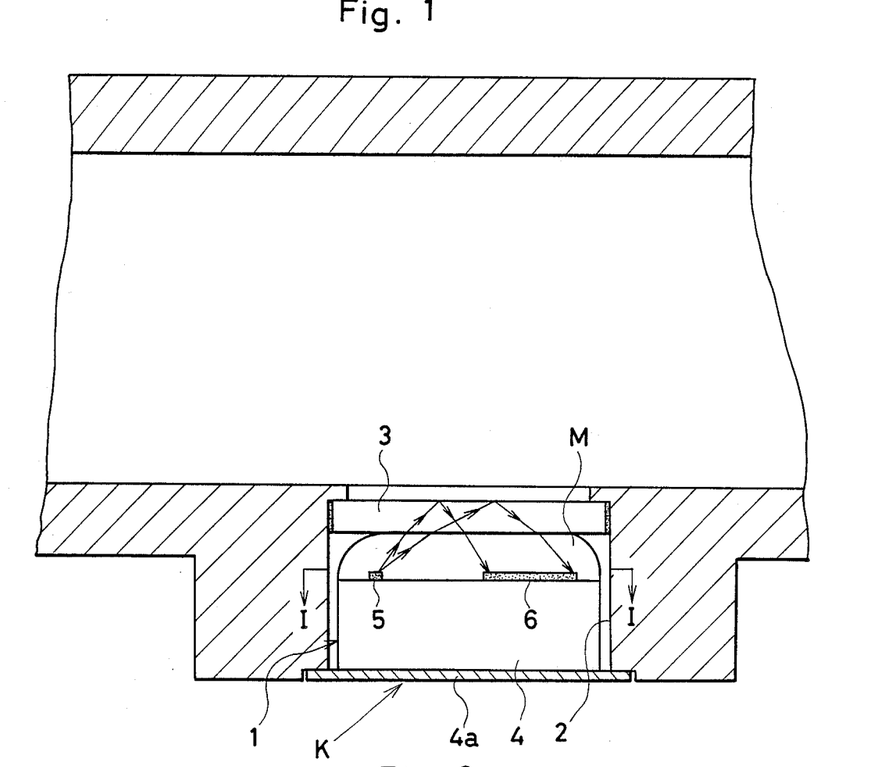
FIG. 1 is a longitudinal cross sectional view of a detector device.
Figure 2:
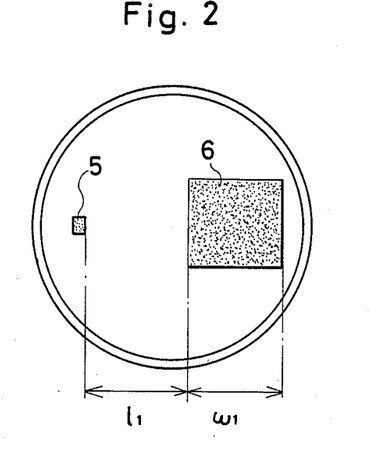
FIG. 2 is a latitudinal view along I—I line of FIG. 1.
Figure 5:
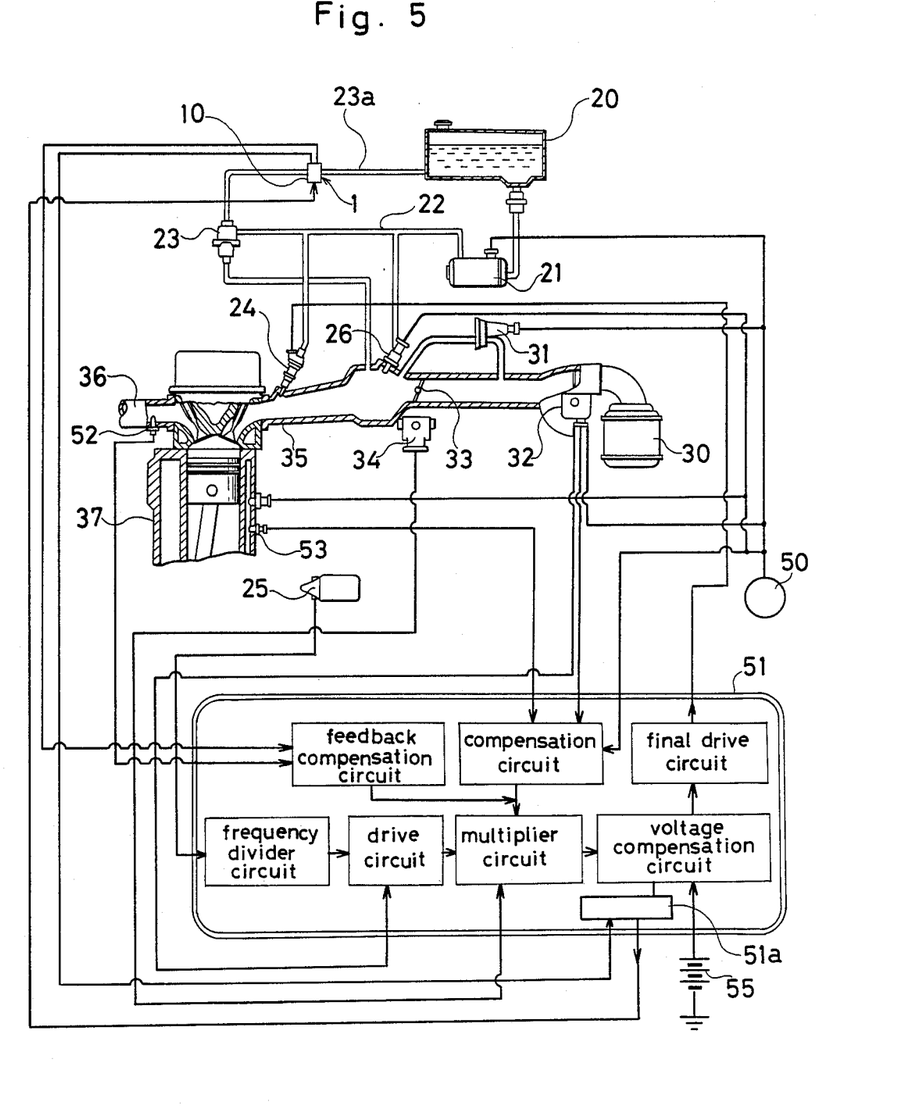
FIG. 5 is a systematic view of an internal combustion engine in use for motor vehicle.

Referring to FIGS. 1 and 2 of the drawings, numeral 1 designates a detector device according to this invention which is placed into an intermediate pipe 23a between a fuel reservoir 20 and a pressure regulator 23 as elucidated hereafter in FIG. 5. The pipe 23 has an aperture 2 at its circumferential wall to communicate the innerside space and outside atmosphere. To the aperture 2, is a flat-shaped flint glass 3 liquid-tightly disposed as an optical permeable plate, outer surface of which is in direct contact with a mixing liquid of gasoline and alcohol flowing through the pipe 23a. In parallel relationship with the flint glass 3, is a pedestal 4 placed, on which a light emitting diode 5 and a photo diode 6 are arranged in coplanar relationship. The light emitting diode 5 and the photo diode 6 are molded in integral with a transparent epoxy resin (M) to fill a space between the glass 3 and the pedestal 4, excluding a pneumatic layer to remain. In an opposite side to the diodes 5,6, is a mounting plate 4a secured to the pedestal 4, the outer peripheral of the plate 4 is fixed to that of the aperture 2 by means of welding or the like.

Figure 3:
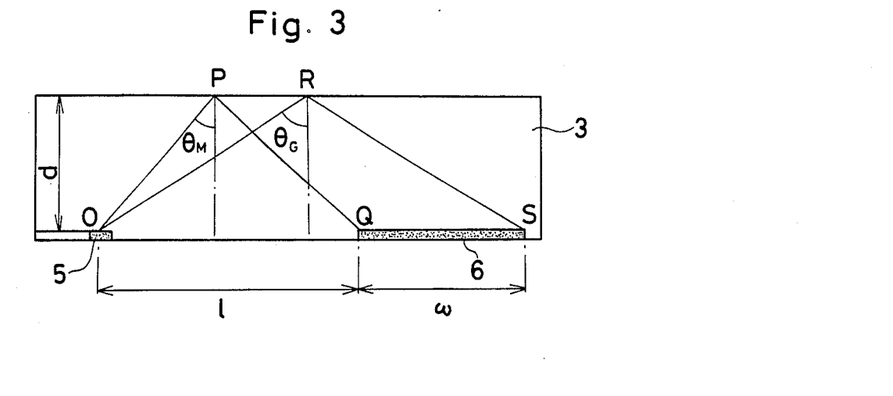
FIG. 3 and FIG. 4 are views shown for the purpose of elucidating a principal.

In determining dimension of the photo diode 6 and a distance between the light emitting diode 5 and photo diode 6, a principle shown in FIG. 3 is employed. As seen in FIG. 3, a distance OQ is a value measured when light beams from a point (O) of the light emitting diode 5 permeate into the glass 3 at a critical angle $\theta M$ to reach at a point (P) of a boundary between the glass 3 and the mixing liquid, reflecting to fall on a point (Q) of the photo diode 6 with a mixing ratio of the liquid as 0:100 (alcohol only).

A distance OS is a value measured when light beams from the point (O) of the light emitting diode 5 permeate into the glass 3 at a critical angle $\theta G$ to reach at a point (R) of the boundary between the glass 3 and the mixing liquid, reflecting to fall on a point (S) of the photo diode 6 with a mixing ratio of the liquid as 100:0 (gasoline only). That is, a distance between the photo diode 6 and the light emitting diode 5 and width dimension of the photo diode 6 along the direction of the distance being determined such as to provide incidental angles ranging from a minimum corresponding to the critical angle when the mixing liquid ratio is at a lower limit of the predetermined range to a maximum corresponding to the critical angle when the mixing liquid ratio is at the upper limit of the predetermined range.

With refraction index of alcohol and gasoline as nM and nG respectively, thickness and optical refraction index of the glass 3 as (d) and (nL), law of reflection expresses the following formulas:

| sin $\Theta M$ = nM/nL | sin$\Theta G$ = nG/nL |
|---|---|
| distance OQ(I) = 2d tan $\Theta M$ | distance OS(I + $\omega$) = 2d tan $\Theta G$ |

From above formulas, inequalities OQ(I)$\leq$2d tan $\theta M$ (1+$\omega$)$\geq$2d tan $\theta G$ are obtained. Accordingly, relationship of 2d tan $\theta M \geq 1 \geq$(2d tan $\theta G - \omega$) is introduced. From the relation, value 1 is determinded by giving $\omega$ a certain dimension since values of tan $\theta M$ and tan $\theta G$ are known.

Thus the values of (I), ($\omega$) are fundamentally determined, however, the glass 3 has the epoxy resin layer (M) thereunder as seen in FIG. 1. In this embodiment, the determination in connection with a width of the photo diode and a distance between the diodes 5,6, are based from the principle of FIG. 4, in which $(d_1)$, $(nL_1)$ designate thickness and refraction index of the epoxy resin layer(M).

Figure 4:
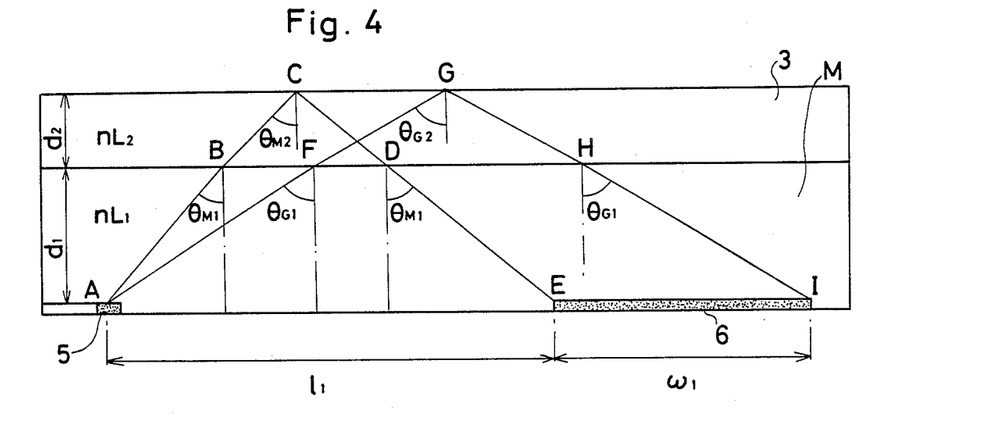

Further, denotation $(\theta M_1)$ shows a critical angle when light beams incident on a boundary between the epoxy resin layer (M) and alcohol, begin to totally reflect at the first time, $(\theta G_1)$ being a critical angle when light beams incident on a boundary between the epoxy resin layer (M) and gasoline, begin to totally reflect at the first time, while $(\theta M_2)$ shows a critical angle when light beams incident on a boundary between the glass 3 and alcohol, begin to totally reflect at the first time, $(\theta G_2)$ being a critical angle when light beams incident on a boundary between the glass 3 and gasoline, begin to totally reflect at the first time. From law of light reflection, sin $\theta M_1 = nM/nL_1$ sin$\theta M_2 = nM/nL_2$ sin $\theta G_1 = nG/nL_1$ sin $\theta G_2 = nG/nL_2$ are obtained.

In connection with the light path A,B,C,D,E of FIG. 4, $AE = 2d_1$ tan $\theta_{M1} + 2d_2$ tan $\theta M_2$ is obtained, while $AI = 2d_1$ tan $\theta G_1 + 2d_2 \tan \theta G_2$ being obtained from the light path A,F,G,H,I. From these expressions, the following relations are obtained.

That is, $I_1 \leq 2d_1$ tan $\theta M_1 + 2d_2$ tan $\theta M_2$ $(I_1 + \omega_1) \geq 2d_1$ tan $\theta G_1 + 2d_2$ tan $\theta G_2$, leading those relations to an inequality $2d_1$ tan $\theta M_1 + 2d_2$ tan $\theta M_2 \geq I_1 \geq 2d_1$ tan $\theta G_1 + 2d_2$ tan $\theta G_2 - \omega_1$. Where dimension $I_1$ is equivalent to a distance expressed by AE, dimension $(\omega_1 + I_1)$ being to a distance expressed by AI.

Thus enabling to introduce a distance $(I_1)$ between the light emitting diode 5 and the photo diode 6 by giving a certain value to the width $(\omega_1)$ of the photo diode 6.

Now FIG. 5 shows a control system in which a detector device according to this invention is associated with an internal combustion engine for motor vehicle. In FIG. 5, numeral 37 designates an engine cylinder, numeral 50 being an ignition key, numeral 51 being a control circuit, numeral 55 a battery cell serving as a power source, numeral 20 a fuel reservoir. Numeral 21 designates a fuel pump, numeral 23 being a pressure regulator which is introduced from the fuel reservoir 20 by way of the intermediate pipe 23a which the detector device 1 is mounted. Numeral 24 shows an injector, numeral 26 being a cold start injector, numeral 25 being an ignition coil, numeral 30 an air cleaner, numeral 31 an air valve, numeral 32 an air flow meter, numeral 33 a throttle valve, numeral 34 a position sensor for the throttle valve 33, numeral 35 an intake pipe, numeral 36 an exhaust pipe, numeral 52 a sensor for detecting air-fuel ratio of the fuel, numeral 53 a temperature sensor for a water cooler circulating in a jacket of the engine cylinder 37.

Figure 6:
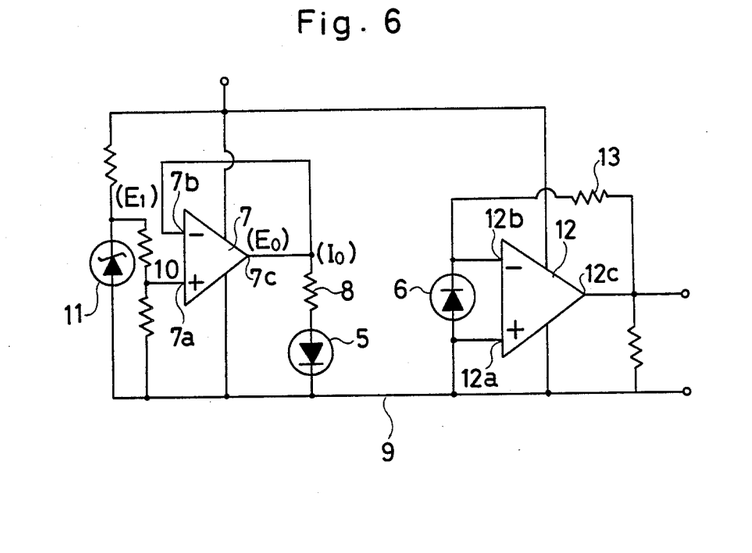
FIG. 6 is a wiring diagram of a compensation circuit.

In FIG. 6 which shows an electronic circuit into which the light emitting diode 5 and the photo diode 6 are incorporated, numeral 7 designates an operational amplifier which connects a negative terminal 7b to an output terminal 7c, and at the same time, connecting it to a common line 9 through an electrical resistance 8 and a light emitting diode 5. A positive terminal 7a of the amplifier 7 is connected to the common line 9 through an electrical resistance 10 and a zener diode 11. The zener diode 11 works so that a constant input voltage $(E_1)$ and a constant output voltage $(E_0)$ are maintained at the positive terminal 7a of the amplifier 7. An output current $(I_0)$ at a joint between the output terminal 7c and the electrical resistance 8, changes depending upon a voltage drop degree of the light emitting diode 5. That is, an elevated ambient temperature works to decrease a voltage drop of the light emitting diode 5 so as to increase the output current $(I_0)$. A reduced ambient temperature works to increase a voltage drop of the light emitting diode 5 so as to decrease the output current $(I_0)$. This allows to supply a current to the light emitting diode 5, the intensity of the current being adjusted to compensate the optical change of the light emitting diode 5 so as to insure temperature compensation effect.

In so doing, an operational amplifier 12 has the photo diode 9 connected between its positive terminal 12a and negative terminal 12b. The positive terminal 12a is connected to the common line 9 while the negative terminal 12b being to an output terminal 12c through an electrical resistance 13. Across the output terminal 12c and the common line 9, is the control circuit 51 connected through an output arrangement 51a.

In operation, an actuation of the ignition key 50 allows to activate the engine, and at the same time, supplying a power source to the control circuit 51. In combination with the activated control circuit 51, the mixing liquid fuel of gasoline and alcohol in the reservoir 20 is supplied to the injector 24 through a fuel pipe 22 by means of fuel pump 21. At this time, the injector 24 works to supply the fuel to the intake pipe 35 at the most appropriately quantity calculated to the operating condition of the engine.

In the meantime, the control circuit 51 impresses a voltage across the light emitting diode 6 to emit light beams which passes through the synthetic resin layer (M) and the glass 3 to reach a boundary between the glass 3 and the mixing liquid fuel. The light beams reached at the boundary with an incident angle as more than a critical angle, reflects to pass back the glass 3 and the resin layer (M) so as to fall on the photo diode 6 which produces an output supplied to the control circuit 50 through the input arrangement 51a.

In this situation, variation of mixing ratio of the fuel liquid changes its refraction index to cause change of the critical angle when the light beams permeate through the glass 3 to reflect at the boundary. The change of the critical angle influences on the quantity of the light beams fell on the photo diode 6 to change the output produced therefrom. The relationship between the mixing ratio of the liquid and the quantity of the light beams fell on the photo diode 6, are previously obtained as data from the change of the refraction index of the mixing liquid to be stored by the control circuit 51.

In so doing, the output from the photo diode 6 allows the control circuit 51 to calculate the most appropriate quantity of injection fuel so as to maintain maintain a good output of the engine.

With the structure thus described, the light emitting diode 5 and the photo diode 6 is located at the position of identical side, so that thickness dimension of the detector device 1 is reduced. The width of the photo diode 6 and distance between diodes 5, 6 are such that the lengthwise dimension is minimized to make a whole structure compact. The width of the photo diode 6 is reduced to minimum size necessary, enabling to contribute cost-saving structure. The casing required to encase the diodes 5,6 is a unitary one to reduce the number of assembly processes so as to facilitate assembly, conducive to an improved production.

Furthermore, in opposition to the counterpart in which a detector device projects into inside of an intermediate pipe, the detector device 1 is substantially immune to a flow resistance of the mixing liquid which is running through the pipe 23a.

Figure 7:
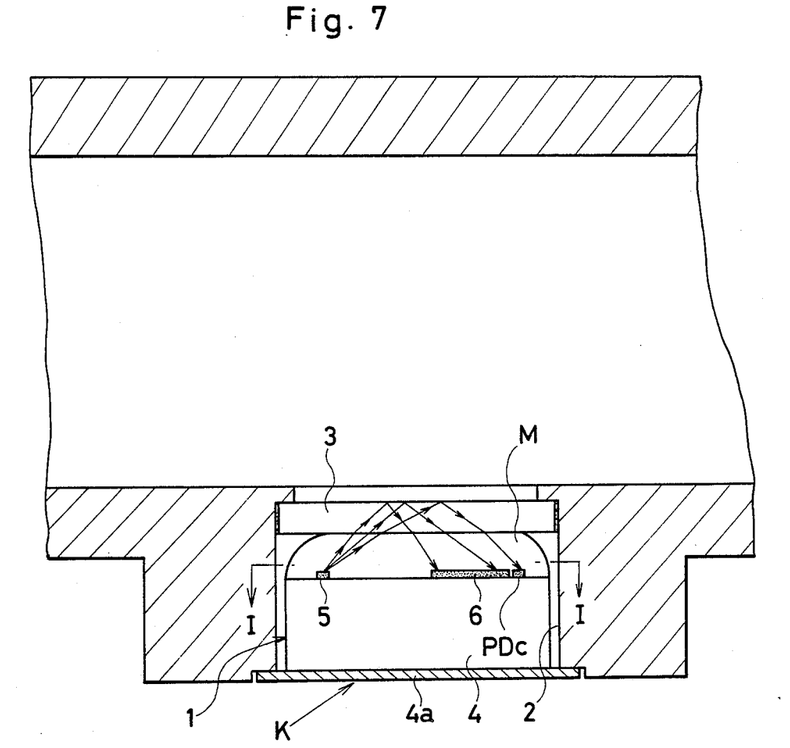
FIG. 7 is a view corresponding to FIG. 1.
Figure 8:
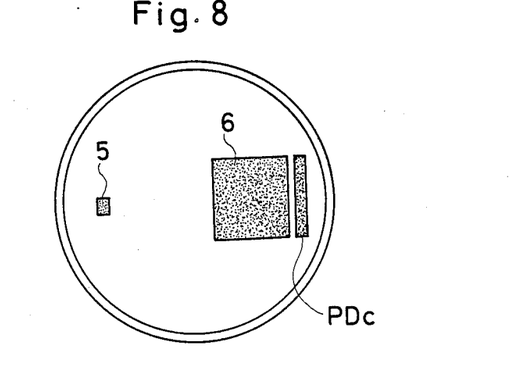
FIG. 8 is a view corresponding to FIG. 2.
Figures 9, 10:
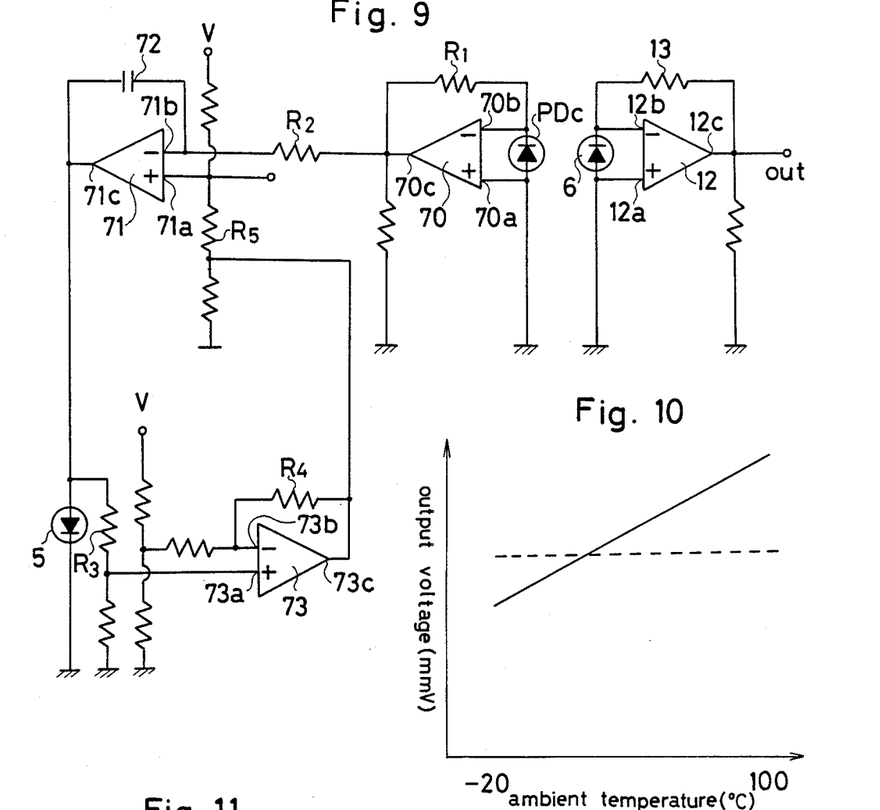
FIG. 9 is a wiring diagram of an electronic circuit.
FIG. 10 is a graph showing a relationship between an output (V) of a photo diode and its ambient temperature (T)

FIGS. 7 through 9 show second embodiment of this invention in which a temperature compensation photo diode (PDc) is discretely provided on the pedestal 4. The diode (PDc) is in the shape of elongated chip, and located opposite to the light emitting diode 5 to be in the neighborhood of the photo diode 6. The location of the diode (PDc) is such that the diode (PDc) receives the light beams only incident on the boundary at more than a critical angle so as to always maintain a constant quantity of the light beams received, regardless of the mixing ratio of the liquid.

The temperature compensation photo diode (PDc) is incorporated into an electronic circuit shown in FIG. 9 in which a wiring connection of the photo diode 6 is similar to that of FIG. 6. The diode (PDc) is connected across positive and negative terminals 70a, 70b of first operational amplifier 70. A common point of the negative terminal 70b and the diode (PDc) is connected to an output terminal 70c of the amplifier 70 by way of an electrical resistance R1. The output terminal 70c is connected to a negative terminal 71b of second amplifier 71 through an electrical resistance R2, across the negative terminal 71b and the output terminal 71c is a condenser 72 connected to prevent an adverse hunting action. A common point of the condenser 72 and the output terminal 71c is grounded by way of the light emitting diode 5. Further, a common point of the output terminal 71c and the light emitting diode 5 is connected to a positive terminal 73a of third operational amplifier 73 through an electrical resistance R3, the amplifier 73 connecting a negative terminal 73b to an output terminal 73c through an electrical resistance R4. A common point of the resistance R4 and the output terminal 73c returns to the second operational amplifier 71 so as to be connected to the positive terminal 71a by way of an electrical resistance R5.

Figure 11:
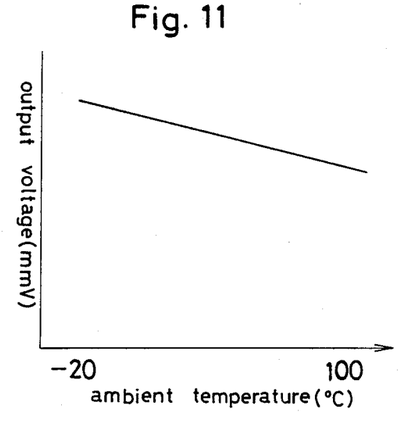
FIG. 11 is a graph showing a relationship between an output (V) of a light emitting diode and its ambient temperature (T)

Under a constant voltage at the positive terminal 71a, the amplifier 71 works to control a quantity of current supplied to the light emitting diode 5 so as to hold the diode (PDc) at a predetermined output level, and leading to a uniform output of the photo diode 6 unless the liquid of gasoline and alcohol changes its refraction index. The refraction of the liquid, however, changes in accordance with the ambient temperature so that the relationship between temperature (T) and output (V) of the photo diode 6 is as seen at solid line in FIG. 10. The relationship between the ambient temperature (T) and voltage drop (V) across the terminals of the light emitting diode 5, is as seen in FIG. 11, so that the voltage drop (V) decreases with the increase of the ambient temperature (T).

Figure 12:
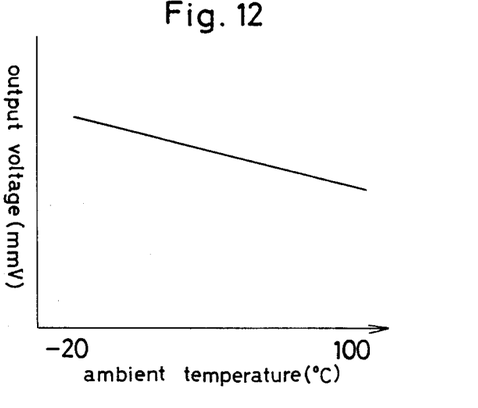
FIG. 12 is a graph showing a relationship between a voltage (V) applied to second amplifier and its ambient temperature (T)

In so doing, the voltage impressed across the terminals of the light emitting diode 5, is forwarded to the third operational amplifier 73 through the positive terminal 73a, so that the amplifier 73 allows the output terminal 73c to produce voltage (V) decreasing with the increase of the ambient temperature as depicted in FIG. 12. The voltage (V) thus changing, is applied to the light emitting diode 5 through the output terminal 71c of the amplifier 71 to act the diode 5 to decrease its light emitting degree. This leads to working to decrease the output of the photo diode 6 so that the output of the photo diode 6 is maintained substantially at a certain level as seen by broken lines in FIG. 10 irrespective of the ambient temperature.

In addition, the light emitting diode 5 deteriorates with a long period of use, in such a degree that the light intensity reduces by a few percent with a thousand operating hours, and reducing by ten or twenty percent with ten thousand operating hours. The quantity of the light beams which the temperature compensation photo diode (PDc) receives, reduces to lower the output, decreasing the output of the first operational amplifier 70. The decreased output of the first amplifier 70 is applied to the negative terminal 71b of the second operational amplifier 71 to be amplified. The amplified output is forwarded through the output terminal 71c to apply it across the light emitting diode 5 to compensate for the loss of the light emitting quantity.

With a long period of use, deposit appears on the surface of the glass 3 to cloud the glass, absorbing the light beams from the diode 5 so as to reduce the quantity of the light beams which the photo diode (PDc) receives. The the light beams lost by the absorption, is compensated in the same manner as the above case in which the light emitting diode 5 is deteriorated.

Figure 13:
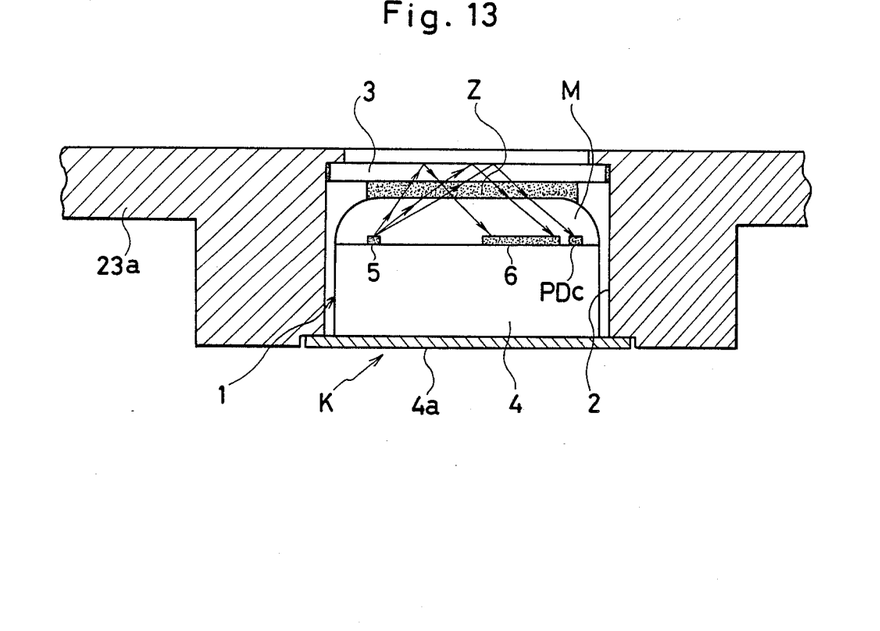
FIG. 13 is a view corresponding to FIG. 1.

It is appreciated that between the glass 3 and the resin layer (M), an optical permeable means such as an oil or silicone may be provided as shown at notation (Z) in FIG. 13 with a view to completely excluding a pneumatic space to develop therebetween. The oil or the silicone is selected because these are greater than the mixing liquid of gasoline and alcohol in optical refraction index.

Further, it is noted that a silicone may be employed instead of the epoxy resin layer (M), instead of the flint glass 3, a reinforced glass or a corrosion resistant plastics may be employed.

Furthermore, it is appreciated that a mixing liquid fuel, is not confine only to gasoline and alcohol.

In addition, it is noted that the detector device according to this invention may be incorporated into a monitor device in which concentration of sugared water and saline water is being continuously detected. This may has an significance particularly in the circle of food industry.

Moreover, the width determination of the photo diode 6 and the distance of the two diodes 5 and 6 may be determined such to provide incidental angles ranging from a minimum corresponding to the critical angle when the alcohol component is at 30 percent within the range 30-60 percent to a maximum corresponding to the alcohol component is at 60% within the above range.

What is claimed is:

1. A detector device for mixing ratio of gasoline and alcohol or the like comprising:
    an optically permeable plate, one side of which is placed to be in direct contact with mixing liquid of different kinds of components;
    a light emitting diode located at other side of said optically permeable plate to be opposite to said mixing liquid, so that light beams emitted from said diode enter said optically permeable plate to be incident on a boundary between said plate and said mixing liquid, the light beams incident on said boundary at less than a critical angle being refracted toward said mixing liquid, while the light beams incident on said boundary at more than the critical angle being totally reflected, said critical angle depending on a degree of said mixing liquid;
    a photo diode having a rectangular shape, and located in coplanar relationship with said light emitting diode to receive the light beams totally reflected from said boundary to generate an output in accordance with the light beams received; and
    a distance between said photo diode and said light emitting diode, and width dimension of said photo diode along the direction of said distance being determined such as to provide incident angles ranging from a minimum corresponding to the critical angle when said mixing liquid ratio is at a lower limit of the predetermined range to a maximum corresponding to the critical angle when said mixing liquid ratio is at upper limit of the predetermined range.

2. A detector device as recited in claim 1, in which relationship between width of said photo diode and said distance of said two diodes, is expressed as follows:

$$2d \cdot \tan(\theta M) \geq 1 \geq (2d \tan(\theta G) - \omega)$$

where
  d: thickness dimension of the optically permeable plate,
  l: distance measured from the center of the light emitting diode to the nearest edge of the photo diode,
  $\omega$: width dimension of the photo diode,
  $\theta M$: a minimum corresponding to the critical angle when the mixing liquid ratio is at lower limit of the predetermined range,
  $\theta G$: a maximum corresponding to the critical angle when the mixing liquid ratio is at upper limit of the predetermined range.

3. A detector device as recited in claim 1, in which said light emitting and said photo diodes are molded integral with a transparent epoxy resin to fill a space between said optically permeable plate and the coplanar surface of said two diodes, the light beams of said light emitting diode passing through the epoxy resin to be incident on the boundary between said optically permeable plate and said mixing liquid, the light beams totally reflected from said boundary passing through said optically permeable plate to fall on said photo diode.

4. A detector device as recited in claim 3, in which relationship between width of said photo diode and said distance of said two diodes, is expressed as follows:

$$2d_1 \cdot \tan(\theta M_1) + 2d_2 \tan(\theta M_2) \geq l_1 \geq 2d_1 \cdot \tan(\theta G_1) + 2d_2 \tan(\theta G_2) - \omega_1$$

where,
  $d_1$: thickness imension of the optically permeable plate,
  $d_1$: thickness dimension of the epoxy resin,
  $l_1$: distance measured from the center of the light emitting diode to the nearest edge of the photodiode,
  $\omega_1$: width dimension of the photo diode,
  $\theta M_1$: a minimum corresponding to the critical angle regarding to the epoxy resin when the mixing liquid ratio is at lower limit of the predetermined range,
  $\theta G_1$: a maximum corresponding to the critical angle regarding to the epoxy resin when the mixing liquid ratio is at upper limit of the predetermined range.
  $\theta M_2$: a minimum corresponding to the critical angle regarding to the optically permeable plate when the mixing liquid ratio is at lower limit of the predetermined range,
  $\theta G_2$: a maximum corresponding to the critical angle regarding to the optically permeable plate when the mixing liquid ratio is at upper limit of the predetermined range.

5. A detector device as recited in claim 1 wherein said optically permeable plate is made of flint glass.

6. A detector device as recited in claim 1 wherein said mixing liquid components are gasoline and alcohol in use for internal combustion engine.

7. A detector device as recited in claim 1 in which a temperature compensation photo diode is provided to receive light beams reflected from said boundary, and incorporated into an electrical circuit to maintain a constant output of said temperature compensation photo diode by controlling a current supply to said light emitting diode.

* * * * *